United States Patent [19]

Trybulski et al.

[11] Patent Number: 5,025,099
[45] Date of Patent: Jun. 18, 1991

[54] (3-AMINO-1-PROPYNYL)METHYLTHIOTHIOPHENE DERIVATIVES

[75] Inventors: Eugene J. Trybulski, Park Ridge, N.J.; Herbert J. Brabander, Nanuet, N.Y.

[73] Assignee: American Cyanamid Company, Stamford, Conn.

[21] Appl. No.: 474,574

[22] Filed: Feb. 2, 1990

[51] Int. Cl.$^5$ ............................................. C07D 409/06
[52] U.S. Cl. .................................... 548/527; 546/212; 549/65
[58] Field of Search ....................... 546/212; 548/527; 514/326, 422, 445; 549/65

[56] References Cited

U.S. PATENT DOCUMENTS 4,005,095  1/1977  Robba et al. ...................... 548/527
4,208,423  6/1980  Pfister ................................ 514/409
4,755,527  7/1988  Stout et al. ......................... 514/422
4,833,139  5/1989  Martin ................................ 514/422

Primary Examiner—Frederick E. Waddell
Assistant Examiner—Ba K. Trinh
Attorney, Agent, or Firm—Kenneth J. Dow

[57] ABSTRACT

Pharmaceutical compounds and compositions which may be represented by the following structural formula:

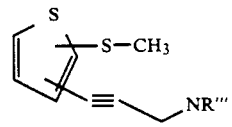

wherein NR''' is selected from amino, ($C_1$-$C_6$) alkylamino, dialkylamino or trialkylamino, pyrrolidino or piperidino. The compounds and compositions are useful in treating central cholinergic dysfunction in mammals.

5 Claims, No Drawings

(3-AMINO-1-PROPYNYL)METHYLTHIOTHIOPHENE DERIVATIVES

BACKGROUND OF THE INVENTION

The present invention relates to novel (3-amino-1-propynyl)methylthiothiophene compounds, pharmaceutical compositions containing the compounds and to the use of the compounds for the treatment of central cholinergic dysfunction.

Senile Dementia of the Alzheimer's type (SDAT) is a neurodegenerative disease which results in the progressive impairment of memory. Post mortem autopsies of brain tissue from SDAT patients have shown a marked decrease in cholinergic neurons. Taken together these observations form the basis for the cholinergic hypothesis of memory loss. A series of chemical synthesis projects have been initiated in the geriatric program to discover selective cholinergic agonists to ameliorate the symptoms of this degenerative disease.

In this respect, a number of derivatives of the cholinergic agent, oxotremorine, have been synthesized. Resul, B. and co workers, Eur. J. Med. Chem., 1982, 17, 317 report the synthesis of N-methyl-N-(1-methyl-4-pyrrolidino-2-butynyl)acet-amide, referred to as BM-5, which acts as an antagonist at some muscarinic sites while being an agonist at most others. It has been suggested that this type of compound may be useful for the therapy of Alzheimer-type dementia.

SUMMARY OF THE INVENTION

This invention is concerned with new compounds described by the following formula 1:

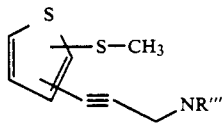

wherein NR''' is selected from NR' and NR'' wherein NR' is selected from amino, ($C_1$-$C_6$) alkylamino, ($C_1$-$C_6$) dialkylamino, pyrrolidino or piperidino; NR'' is ($C_1$-$C_6$) trialkylamino; and their pharmaceutically acceptable acid addition salts. The invention is also concerned with methods of treating diseases of the central nervous system in mammals employing these new compounds; with pharmaceutical preparations containing these compounds; and with the processes for the production of these compounds.

DESCRIPTION OF THE INVENTION

The novel compounds of the present invention may be prepared in accordance with the following Scheme I, wherein NR' is selected from amino, ($C_1$-$C_6$) alkylamino, ($C_1$-$C_6$) dialkylamino, pyrrolidino, or piperidino, and NR'' is ($C_1$-$C_6$) trialkylamino; $R^{IV}Z$ is ($C_1$-$C_6$) alkyl halide and X is bromine or iodine.

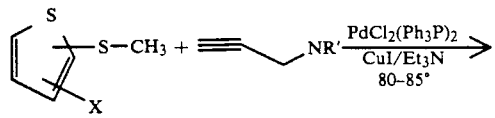

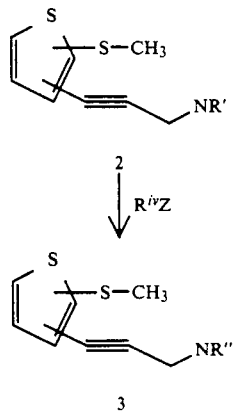

The synthesis of 3-substituted-2-(methylthio)-thiophene, 3-substituted-4-(methylthio)thiophene or 2-substituted-3-(methylthio)thiophene is accomplished by palladium (0) catalyzed coupling reactions between the appropriate propargyl amine and a 3-halo-2-(methylthio)thiophene, 3-halo-4-(methylthio)thiophene or a 2-halo-3-(methylthio)thiophene in the presence of a base such as a tertiary amine and a cuprous halide at the reflux temperature for several hours, giving the desired product. All amines form appropriate acid addition salts in the expected manner.

Reaction of the amine product NR' with a ($C_1$-$C_6$) alkyl halide gives the quarternary ammonium salt where NR'' is ($C_1$-$C_6$) trialkylamino.

The novel compounds described herein are useful as cholinergic agents. A chronic deficiency in central cholinergic function has been implicated in a variety of neurologic and psychiatric disorders, including Senile Dementia of the Alzheimer's type (SDAT), tardive dyskinesia, Pick's disease and Huntington's chorea. Post mortem neurochemical investigations of patients with SDAT have demonstrated a reduction in presynaptic markers for acetylcholine-utilizing neurons in the hippocampus and the cerebral cortex. [P. Davies and A. J. R. Maloney, Lancet, 1976-II, 1403, (1976); E. K. Perry, R. H. Perry, G. Blessed, B. E. Tomlinson, J. Neurol. Sci., 34, 247, (1976)]. The basis for this cholinergic abnormality is unclear, but evidence suggests that the cholinergic neurons in the neucleus basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy could be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)] and oxotremorine [R. T. Bartus, R. L. Dean, B. Beer, Psychopharmacology Bulletin, 19, 168, (1983)] produced significant improvement in performance. These results in aged monkeys were corroborated in SDAT patients with arecoline which produced a more-consistent improvement when compared to the anticholinesterase inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cereberal cortex. However, the search must be refined to seek agonists which will not effect significantly the remaining body cholinergic functions. The recent disclosure (T. I. Bonner, N. J. Buckley, A. C. Young, M. R. Brann, Science, 237,527, (1987)] that muscarinic receptors are not all the same but exist as a heterogenous population of receptors substantiates the possibility for the discovery of a selective muscarinic agonist.

N-methyl-N-(1-methyl-4-pyrrolidino-2-butynyl-)acetamide (BM-5) has been reported to be a presynaptic cholinergic antagonist (which should disinhibit the release of endogenous acetylcholine) and a postsynaptic partial cholinergic agonist (which should mimic the effects of acetylcholine).

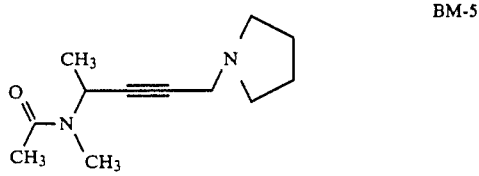

BM-5

Chemically, BM-5 is a flexible molecule that can assume a number of different conformations. The present invention describes the synthesis of a series of (3-amino-1-propynyl)methylthiothiophenes which are derivatives of BM-5 in which one degree of rotational freedom (bond c) has been restricted. Connection of the N-methyl group to the butynyl methyl group in BM-5 by the addition of a methylene fragment generates compound 4. Aromatization of the acetylated pyrrolidino ring in 4 generates 5. Substitution of a thiophene ring for the pyrrole ring and the thiomethyl group for the acetyl functionality provides compounds of general formula 1, which represent the target molecules of this invention.

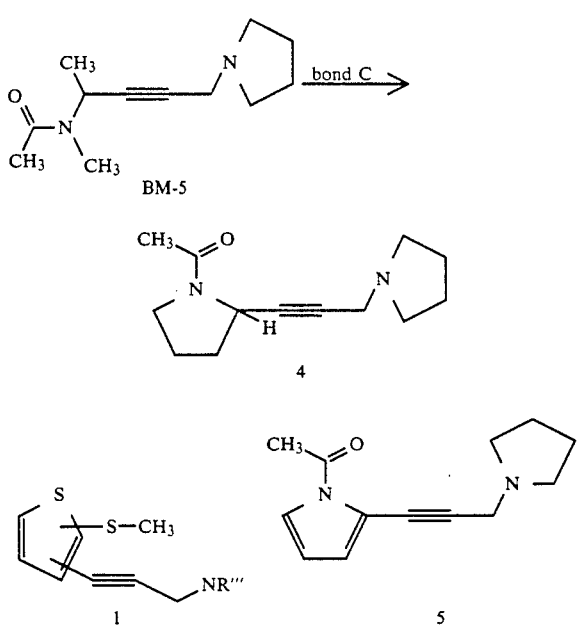

Scheme I

The compounds of this invention were tested for cholinergic activity according to the following procedures.

[$^3$H] Quinuclidinyl Benzilate Binding Assay

This assay is utilized in conjunction with the $^3$H-cis-methyldioxolane binding assay to evaluate antagonist and high affinity agonist binding properties of CNS cholinergic agents. The procedure is adapted from Watloson, M., Yamamura, H. I., and Roeske, W. R., J. Pharmacol. Exp. Ther. 237: 411-418 (1986) and Watson, M., Roeske, W. R., and Yamamura, H. I., J. Pharmacol. Exp. Ther. 237: 419-427 (1986).

Tissue Preparation

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds

A stock solution of atropine is prepared at 0.2 mM to define non-specific binding (1 μM final conc). Test compounds are prepared at 40 mM (final conc 1 mM) in buffer (if Water soluble) or in absolute ethanol—1N HCl (1:1, v/v) and serially diluted to the desired concentrations. In general, dose-response profiles are examined between 1 mM and 1 pM final concentrations.

Preparation of $^3$H-QNB $^3$H-QNB (NEN, NET-656; specific activity=30.0 Ci/mmol) is diluted to 5 nM, with NaPB (final concentration=0.25 nM activity -18,000 cpm at a counting efficiency of 55%).

$^3$H-QNB Binding Assay

A typical protocol is outlined below:

| Tube No. | ID* | Buffer μL | Atropine μL | Test Compound μL | $^3$H-QNB μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | - | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 125 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand over night, shaken and then counted. Specific binding is calculated as Total−NS (non-specific). The percent inhibition of specific binding is then calculated and the IC50 values computed using either the LIGAND or LUNDON software packages for competition binding. The results of this test on representative compounds of this invention appear in Table I.

[$^3$H]-Cis-methyldioxolane Binding Assay (High Affinity)

This assay is utilized in conjunction with $^3$H-QNB binding to evaluate high affinity agonist binding and antagonist properties of CNS cholinergic agents. The procedure is adapted from Vickroy, T. W., Roeske, W. R., and Yamamura, H. I., J. pharmacol. Exp. Ther. 229: 747–755 (1984). This is a rapid filtration assay that is set up to label only the high affinity agonist conformation of the muscarinic cholinergic receptor.

Tissue Preparation

Rats are sacrificed by decapitation and the brain removed and placed on ice. The cerebral cortex is dissected on a cold stage, weighed and homogenized (Polytron, setting 5.5 with Pt-10 saw-tooth generator for 15 seconds in 50 volumes (wet wt/vol) of ice-cold 10 mM (8.1 mM Na$_2$HPO$_4$, 1.9 mM KH$_2$PO$_4$ sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:300 (original Wet wt/vol) With ice-cold NaKPB for use in the assay. The final protein content per 2.0 ml of incubation mixture is 0.75 mg.

Dilution of Compounds

A stock solution of Atropine is prepared at 0.2 mM to define non-specific binding 1 μM final conc). Test compounds are prepared at 40 mM (final conc 1 mM) in buffer (if Water soluble) or in absolute ethanol—1N HCl (1:1, v/v) and serially diluted to the desired concentrations. In general, dose-response profiles are examined between 1 mM and 1 pM final concentrations.

Preparation of $^3$H-CD $^3$H-CD (NEN, NET-647; specific activity=55.5 Ci/mmol) is diluted to 20 nM with NaPB (final conc=1.0 nM, activity - 75,000 cpm at a counting efficiency of 55%).

Technical Notes $^3$H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding)are always measured on single PEI treated filter strips to minimize filter-to-filter variability. (See Bruns, R. F., et al. Anal. Biochem. 132: 74–81 (1983) !or the use of PEI treated filters in filtration receptor assays).

The $^3$H-CD is prepared fresh in buffer just prior to use in the assay to avoid possible decomposition. It should be kept on an ice bath after dilution in buffer.

$^3$H-CD Binding Assay

A typical protocol is outlined below:

| Tube No. | ID* | Buffer μL | Atropine μL | Test Compound μL | $^3$H-CD μL | Tissue ml |
|---|---|---|---|---|---|---|
| 1–2 | Total | 50 | — | — | 100 | 1.85 |
| 3–4 | NS | 40 | 10 | — | " | " |
| 5–6 | 4e–11 | — | — | 50 | " | " |
| 7–8 | 4e–10 | — | — | " | " | " |
| 9–10 | 4e–09 | — | — | " | " | " |
| 11–12 | 4e–08 | — | — | " | " | " |
| 13–14 | 4e–07 | — | — | " | " | " |
| 15–16 | 4e–06 | — | — | " | " | " |
| 17–18 | 4e–05 | — | — | " | " | " |
| 19–20 | 4e–04 | — | — | " | " | " |
| 21–22 | 4e–03 | — | — | " | " | " |
| 23–24 | 4e–02 | — | — | " | " | " |

*Stock concentration [M] of compound to be tested.

Components are added in the following order: compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through PEI pretreated GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total−NS (non-specific). The percent inhibition of specific binding is then calculated and the IC50 values computed using either the LIGAND or LUNDON software packages for competition binding. The results of this test on representative compounds of this invention appear in Table I.

TABLE I

| Compound | $^3$H-QNB IC$_{50}$ μM | $^3$H-CD IC$_{50}$ nM |
|---|---|---|
| 1-[3-[4-(Methylthio)-3-thienyl]-2-propynyl]pyrrolidine | 3.34 | 366 |
| 1-[3-[4-(Methylthio)-3-thienyl]-2-propynyl]pyrrolidine, hydrochloride | 2.27 | 110 |
| 1-[3-[4-(Methylthio)-3-thienyl]-2-propynyl]piperidine | 5.35 | 998 |
| 1-[3-[4-(Methylthio)-3-thienyl]-2-propynyl]piperidine | 5.88 | 530 |
| N,N-Dimethyl-3-[4-(methylthio)-3-thienyl]-2-propyn-1-amine, | 239 | 4834 |
| N,N-Dimethyl-3-[4-(methylthio)-3-thienyl]-2-propyn-1-amine, hydrochloride | 67.5 | 1228 |
| N,N,N-Trimethyl-3-[4-(methylthio)-3-thienyl]-2-propyn-1-aminium, iodide | 9.05 | 121 |
| 1-[3-[2-(Methylthio)-3-thienyl]-2-propynyl]pyrrolidine | 0.92 | 31 |
| 1-[3-[2-(Methylthio)-3-thienyl]-2-propynyl]pyrrolidine, hydrochloride | 0.81 | 31 |
| 1-[3-[2-(Methylthio)-3-thienyl]-2-propynyl]piperidine | 1.14 | 31.1 |
| 1-[3-[2-(Methylthio)-3-thienyl]-2-propynyl]piperidine, hydrochloride | 2.2 | 32.5 |
| N,N-Dimethyl-3-[2-(methylthio)-3-thienyl]-2-propyn-1-amine, | 21.4 | 942 |
| N,N-Dimethyl-3-[2-(methylthio)-3-thienyl]-2-propyn-1-amine, hydrochloride | 23.3 | 969 |
| N,N,N-Trimethyl-3-[2-(methylthio)-3-thienyl]-2-propyn-1-aminium, iodide | 3.44 | 52.3 |
| 1-[3-[3-(Methylthio)-2-thienyl]-2- | 1.38 | 16 |

TABLE I-continued

| Compound | $^3$H-QNB IC$_{50}$ μM | $^3$H-CD IC$_{50}$ nM |
|---|---|---|
| propynyl]pyrrolidine | | |
| 1-[3-[3-(Methylthio)-2-thienyl]-2-propynyl]pyrrolidine, hydrochloride | 1.87 | 44 |
| 1-[3-[3-(Methylthio)-2-thienyl]-2-propynyl]piperidine | 1.97 | 122 |
| 1-[3-[3-(Methylthio)-2-thienyl]-2-propynyl]piperidine, hydrochloride | 2.1 | 44 |
| N,N-Dimethyl-3-[3-(methylthio)-2-thienyl]-2-propyn-1-amine, | 35 | 1123 |
| N,N-Dimethyl-3-[3-(methylthio)-2-thienyl]-2-propyn-1-amine, hydrochloride | 40.4 | 1244 |
| N,N,N-Trimethyl-3-[3-(methylthio)-2-thienyl]-2-propyn-1-aminium, iodide | 5.98 | 5.92 |

Those compounds which have $^3$H-CD IC$_{50}$ values of <1000 nM and/or $^3$H-QNB IC$_{50}$ values of <1000 μM are considered active.

In general the compounds show cholinergic agonist activity.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions or manufacture and storage and must be preserved against the contaminating action of microorganisms such as bacteria and fungi. The carrier can be a solvent or dispersion medium containing, for example, water ethanol, polyol (e.g., glycerol, propylene glycol, and liquid polyethylene glycol), suitable mixtures thereof, and vegetable oils.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

General Coupling Reaction

A mixture of 0.031 mole of the appropriate bromo(-methylthio)thiophene prepared as described below in Examples 22 et seq., 20 ml of triethylamine and 0.04 mole of the appropriate 3-amino-1-propyne intermediate is stirred under argon for 5 minutes Seven hundred and fifty milligrams of bis(triphenylphospine) palladium (II) chloride and 450 mg of copper (I) iodide is added and the stirred reation is heated at 80°-85° C. for 3 hours. The reaction mixture is cooled, partitioned between diethyl ether and 65 ml of 10% sodium carbonate, and the layers are separated. The organic layer is filtered thru diatomaceous earth, washed with aqueous sodium chloride and dried over sodium sulfate. The crude product is purified by chromatography using silica gel as absorbent followed by filtration of the product band through a pad of magnesium silicate to give the desired products in 40-65% yields. The purity is determined by $^1$H NMR spectroscopy and by thin layer chromatography. Table III sets forth compounds made by this procedure using suitable starting materials.

TABLE III

| Example # | Product | mp °C. or mass spectrum m/e (MH+) (M/Z) |
|---|---|---|
| 1 | 1-[3-[4-(Methylthio)-3-thienyl]-2-propynyl]-pyrrolidine | MH+ = 238 |
| 2 | 1-[3-[4-(Methylthio)-3-thienyl]-2-propynyl]-pyrrolidine, hydrochloride | 70–72° |
| 3 | 1-[3-[4-(Methylthio)-3-thienyl]-2-propynyl]-piperidine | MH+ = 252 |
| 4 | 1-[3-[4-(Methylthio)-3-thienyl]-2-propynyl]-piperidine, hydrochloride | 132–134° |
| 5 | N,N-Dimethyl-3-[4-(methylthio)-3-thienyl]-2-propyn-1-amine | MH+ = 212 |
| 6 | N,N-Dimethyl-3-[4-(methylthio)-3-thienyl]-2-propyn-1-amine, hydrochloride | 137–139° |
| 7 | 1-[3-[2-(Methylthio)-3-thienyl]-2-propynyl]-pyrrolidine | MH+ = 238 |
| 8 | 1-[3-[2-(Methylthio)-3-thienyl]-2-propynyl]-pyrrolidine, hydrochloride | 150–152° |
| 9 | 1-[3-[2-(Methylthio)-3-thienyl]-2-propynyl]-piperidine | MH+ = 252 |
| 10 | 1-[3-[2-(Methylthio)-3-thienyl]-2-propynyl]-piperidine, hydrochloride | 155–157° |
| 11 | N,N-Dimethyl-3-[2-(methylthio)-3-thienyl]-2-propyn-1-amine | MH+ = 212 |
| 12 | N,N-Dimethyl-3-[2-(methylthio)-3-thienyl]-2-propyn-1-amine, hydrochloride | 130–132° |
| 13 | 1-[3-[3-(Methylthio)-2-thienyl]-2-propynyl]-pyrrolidine | M/Z = 238.0722 |
| 14 | 1-[3-[3-(Methylthio)-2-thienyl]-2-propynyl]-pyrrolidine, hydrochloride | 124–126° |
| 15 | 1-[3-[3-(Methylthio)-2-thienyl]-2-propynyl]-piperidine | M/Z = 252.0882 |
| 16 | 1-[3-[3-(Methylthio)-2-thienyl]-2-propynyl]-piperidine, hydrochloride | 124–126° |
| 17 | N,N-Dimethyl-3-[3-(methylthio)-2-thienyl]-2-propyn-1-amine | M/Z = 212.057 |
| 18 | N,N-Dimethyl-3-[3-(methylthio)-2-thienyl]-2-propyn-1-amine, hydrochloride | 168–170° |

(MH+) = low resolution mass spectrum
(M/Z) = high resolution mass spectrum

General procedure for making aminium, iodides

One point four millimoles of N,N-dimethyl-3 [4-(methylthio)-3-thienyl]-2-propyn-1-amine, N,N-dimethyl-3-[2-(methylthio)-3-thienyl]-2-propyn-1-amine or N,N-dimethyl-3-[2-(methylthio)-2-thienyl]-2-propyn-1-amine is dissolved in 10 ml of diethyl ether, 0.75 ml of methyl iodide is added and the reaction is refrigerated overnight. The crude product is collected, recrystallized from 5 ml of ethanol and cooled. The pure product is collected and dried in vacuo.

The following compounds are made by this procedure.

TABLE IV

| Example # | Product | mp °C. or mass spectrum m/e (MH+) |
|---|---|---|
| 19 | N,N,N-Trimethyl-3-[4-(methylthio)-3-thienyl]-2-propyn-1-aminium, iodide | 177–179° |
| 20 | N,N,N-Trimethyl-3-[2-(methylthio)-3-thienyl]-2-propyn-1-aminium, iodide | 137–139° |
| 21 | N,N,N-Trimethyl-3-[3-(methylthio)-2-thienyl]-2-propyn-1-aminium, iodide | 163–165° |

The procedures for making the intermediate bromothiophenes are described below.

EXAMPLE 22

3-Bromo-4-(methylthio)thiophene

A solution of 27.s g of 3,4-dibromothiophene in 200 ml of dry diethyl ether is cooled to −78° C. Fifty-five ml of n-butyl lithium is added via a syringe and the reaction is stirred for 20 minutes. The resulting solution is transferred via a cannula to an ice cooled solution of 28.1 g of methyldisulfide in 150 ml of diethyl ether and a precipitate is formed immediately. The reaction is stirred at room temperature for one hour, then treated with 150 ml of water. The layers are separated, the diethyl ether layer is washed with water, dried over sodium sulfate and concentrated in vacuo. The residue is purified by Kugelrohr distillation to give 22 g of desired product as a yellow oil, by 60°–100° C. (5 mm Hg).

EXAMPLE 23

3-Bromo-2-(methylthio)thiophene

Following the procedure of Example 22, 23 g of the desired product, as a pale yellow oil, is obtained, by 60°–100° C. (15 mm Hg).

EXAMPLE 24

3-(Methylthio)thiophene

Following the procedure of Example 22, 21 g of desired product, as a pale yellow oil, is obtained, by 80° C. (20 mm Hg).

EXAMPLE 25

4-Bromothiazole

A solution of 15 g of 3-(methylthio)thiophene in 60 ml of acetic acid is stirred and cooled 15° C. Twenty and four tenths grams of N-bromosuccinimide is added in portions at a rate so as to maintain the reaction temperature between 15°–17° C. and the reaction is stirred at room temperature for 2.5 hours. The reaction mixture is treated with 75 ml of water, extracted with 600 ml of diethyl ether, the diethyl ether portion is washed with water and then carefully shaken three times with saturated sodium bicarbonate. The diethyl ether layer is washed again with water, dried over sodium sulfate and concentrated in vacuo. The dark green oil was purified by Kugelrohr distillation to give 19.5 g of a pale yellow-green oil, by 74°–78° C. (0.15 mm Hg).

We claim:

1. A compound selected from the formula:

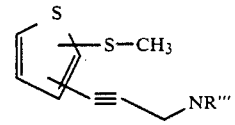

wherein NR''' is pyrrolidino; and the pharmaceutically acceptable acid addition salts thereof.

2. The compound according to claim 1, 1-[3-[4-(methylthio)-3-thienyl]-2-propynyl]pyrrolidine.

3. The compound according to claim 1, 1-[3-[2-(methylthio)-3-thienyl]-2-propynyl]pyrrolidine.

4. The compound according to claim 1, 1-[3-[3-(methylthio)-2-thienyl]-2-propynyl]pyrrolidine.

5. A pharmaceutical composition of matter in dosage unit form comprising from about 1 mg to about 500 mg of a compound selected from those of claim 1 in association with a pharmaceutically acceptable carrier.

* * * * *